United States Patent
Neuteboom et al.

(10) Patent No.: US 10,494,463 B2
(45) Date of Patent: Dec. 3, 2019

(54) ETHYLENE POLYMERS HAVING HIGH DENSITY

(71) Applicant: SABIC Global Technologies B.V., Bergen op Zoom (NL)

(72) Inventors: Peter Neuteboom, Hoensbroek (NL); Franciscus Petrus Hermanus Schreurs, Maastricht (NL); Carolina de los Angeles Toloza Porras, Maastricht (NL); Diego Mauricio Castaneda Zuniga, Maastricht (NL); Jan Nicolaas Eddy Duchateau, Paal (BE)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/738,966

(22) PCT Filed: Jun. 6, 2016

(86) PCT No.: PCT/EP2016/062779
§ 371 (c)(1),
(2) Date: Dec. 21, 2017

(87) PCT Pub. No.: WO2017/001152
PCT Pub. Date: Jan. 5, 2017

(65) Prior Publication Data
US 2018/0171048 A1    Jun. 21, 2018

(30) Foreign Application Priority Data

Jun. 30, 2015 (EP) ................................. 15174486
Jul. 31, 2015 (EP) ................................. 15179267

(51) Int. Cl.
| | | |
|---|---|---|
| *C08F 210/02* | (2006.01) | |
| *C08J 5/18* | (2006.01) | |
| *C08F 232/04* | (2006.01) | |
| *G01N 25/48* | (2006.01) | |
| *G01N 30/00* | (2006.01) | |

(52) U.S. Cl.
CPC ............ *C08F 210/02* (2013.01); *C08J 5/18* (2013.01); *C08F 2500/04* (2013.01); *C08F 2500/17* (2013.01); *C08F 2500/26* (2013.01); *C08L 2207/062* (2013.01); *G01N 25/4866* (2013.01); *G01N 2030/486* (2013.01)

(58) Field of Classification Search
USPC .................................................. 526/64, 308
See application file for complete search history.

(56) References Cited

U.S. PATENT DOCUMENTS

| | | |
|---|---|---|
| 3,383,348 A | 5/1968 | Grasley |
| 3,494,897 A | 2/1970 | Reding et al. |
| 4,029,875 A * | 6/1977 | Gloriod .................. C08F 10/02 526/308 |

FOREIGN PATENT DOCUMENTS

| | | | |
|---|---|---|---|
| CA | 2795843 | * 10/2011 | ............ C08F 210/02 |
| DE | 1519367 A1 | 3/1970 | |
| WO | 2011138400 A1 | 11/2011 | |
| WO | 2017001151 A1 | 6/2016 | |

OTHER PUBLICATIONS

E.M Abdel-Bary (ed.), "Handbook of Plastic Films", Rapra Technology Ltd., 2003, in sections 2.3 and 2.4.
International Search Report dated Sep. 15, 2016; International Appln No. PCT/EP2016/062779; International Filing Date Jun. 6, 2016 (5 pages).
Kaltenbacher, E.J. et al., "The Use of Melt Strength in Predicting the Possibility of Polyethylene Extrusion Coating Resins", Tappi; Jan. 1967, vol. 50, No. 1, p. 20 (1 page).
Peacock, "Handbook of Polyethylene: Structures, Properties, and Applications," Marcel Dekker, Inc. New York, 2000, pp. 43-66.
US Dept. of Labor report OSHA 3373-10, 2009, "Hexavalent Chromium", (32 pages).
Written Opinion dated Sep. 15, 2016; International Appln No. PCT/EP2016/062779; International Filing Date Jun. 6, 2016 (6 pages).

* cited by examiner

*Primary Examiner* — Fred M Teskin
(74) *Attorney, Agent, or Firm* — Cantor Colburn LLP

(57) ABSTRACT

The present invention relates to an ethylene polymer comprising moieties according to Formula (IB): wherein R is a moiety comprising $\geq 1$ and $\leq 10$ carbon atoms; wherein $R^1$ and $R^2$ are each individually hydrogen or a moiety comprising $\geq 1$ and $\leq 5$ carbon atoms, $R^1$ and $R^2$ may be the same or different; wherein the ethylene polymer has a molecular weight distribution of $\geq 3.0$ and $\leq 40.0$; the ethylene polymer has a melting temperature of $\geq 115°$ C.; the ethylene polymer has a density $\geq 935$ and $\leq 960$ kg/m3; the ethylene polymer is essentially free from chromium, hafnium, zirconium and tetrahydrofuran; for the fraction of the ethylene polymer having a molecular weight >100 kg/mol, the intrinsic viscosity of the ethylene polymer is related to the molecular weight according to the inequality: log I.V.<0.65*log M−3.10 Such polymers have high density, high purity and good processability, whilst maintaining barrier properties for oxygen and water vapour at a level similar to high-density polyethylenes produced via catalytic processes.

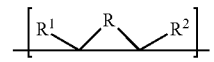

Formula IB

14 Claims, No Drawings

ETHYLENE POLYMERS HAVING HIGH DENSITY

CROSS REFERENCE TO RELATED APPLICATIONS

This application is a 371 of International Application No. PCT/EP2016/062779, filed Jun. 6, 2016, which claims priority to European Application Nos. 15179267.8, filed Jul. 31, 2015 and 15174486.9, filed Jun. 30, 2015 which are incorporated herein by reference in their entirety.

The present invention relates to ethylene polymers having a high density and high purity. The invention further relates to the production of such ethylene polymers. The invention further relates to the use of such ethylene polymers. The invention further relates to polymer compositions and films comprising such ethylene polymers.

Ethylene polymers are well known in the art. There are a great variety of applications in which ethylene polymers find their field of application. A great variety of ethylene polymers are available, having properties rendering them suitable for specific applications. The family of ethylene polymers comprises for example low-density polyethylenes (also referred to as LDPE), linear low-density polyethylenes (also referred to as LLDPE), and high-density polyethylenes (also referred to as HDPE). These types of ethylene polymers are well known in the art. The production processes of these ethylene polymers are for example described in "Handbook of Polyethylene" by Andrew Peacock (2000; Dekker; ISBN 0824795466) at pages 43-66.

One type of ethylene polymers is high-density polyethylene. High-density polyethylenes are polymers that have amongst others certain low permeability to oxygen and water vapour. High-density polyethylenes are commonly produced in catalytic polymerisation processes. The catalyst systems that may be applied in such catalytic polymerisation processes are for example catalyst systems of the Ziegler type, of the Phillips type, and/or of the single-site type. These types of catalyst systems are well known in the art and for example described in Lloyd, L., 'Olefin Polymerization Catalysts', in 'Handbook of Industrial Catalysts', p. 311-350, ISBN: 978-0-387-24682-6, 2011. High-density polyethylenes may for example have a density as measured according to ISO 1183-1 (2012), method A of ≥935 and ≤970 kg/m³.

High-density polyethylenes produced via catalytic polymerisation processes have certain drawbacks. For example, such high-density polyethylenes may contain traces of undesirable compounds originating from the catalyst system used in the production of such high-density polyethylenes.

High-density polyethylenes produced via catalytic polymerisation processes in the presence of catalyst systems of the Ziegler type commonly contain traces of tetrahydrofuran. High-density polyethylenes produced via catalytic polymerisation processes in the presence of catalyst systems of the Phillips type commonly contain traces of chromium. High-density polyethylenes produced via catalytic polymerisation processes in the presence of catalyst systems of the single-site type commonly contain traces of zirconium and/or hafnium.

Chromium is known to have detrimental effects. Chromium compounds, in particular those containing chromium (VI), are suspected carcinogenic and mutagenic, and may cause health problems such as for example allergic reactions, skin rash, nose irritations and nose bleed, ulcers, weakened immune system, and damage to internal organs such as liver and kidney. Both tetrahydrofuran and chromium are undesirable to be present in polymer materials that are intended for use in food contact applications for health reasons. The use of tetrahydrofuran and chromium in the production process of high density polyethylene is also undesirable in view of workers health. This is for example presented in US Dept. of Labor report OSHA 3373-10 2009 'Hexavalent Chromium', which presents the hazards of workers exposed to chromium (VI), and in US Dept. of Labor OSHA report 'Occupational Health Guideline for Tetrahydrofuran', February 1978, which present the hazards of workers exposed to tetrahydrofuran. Tetrahydrofuran is also suspected carcinogenic.

In the context of the present invention, essentially free of tetrahydrofuran means that the ethylene polymer comprises for example at most 40 ppm of tetrahydrofuran, alternatively at most 20 ppm, alternatively at most 10 ppm, alternatively at most 5 ppm, alternatively at most 2 ppm. In the context of the present invention, essentially free of chromium means that the ethylene polymer comprises for example at most 20 ppm of chromium or compounds comprising chromium atoms, alternatively at most 10 ppm, alternatively at most 5 ppm, alternatively at most 2 ppm. In the context of the present invention, essentially free of zirconium means that the ethylene polymer comprises for example at most 20 ppm of zirconium or compounds comprising zirconium atoms, alternatively at most 10 ppm, alternatively at most 5 ppm, alternatively at most 2 ppm. In the context of the present invention, essentially free of hafnium means that the ethylene polymer comprises for example at most 20 ppm of hafnium or compounds comprising hafnium atoms, alternatively at most 10 ppm, alternatively at most 5 ppm, alternatively at most 2 ppm. In the context of the present invention, 'ppm' is to be understood to be the parts per million of weight, being the number of weight units per million weight units of the ethylene polymer.

Such traces may be detrimental for the long-term stability of the ethylene polymer. Also, such traces may render the ethylene polymer unsuitable for certain areas of application where a high purity is required. Such areas of application include for example certain food packaging applications, such as flexible films for packaging of fresh foods such as for example fruit juices, dairy products, meat, cheese, fish, fruits, vegetables and/or baked goods. High-density polyethylenes produced via catalytic polymerisation processes may lack the level of purity that is required for such applications. Increasingly stringent regulations in the field of product health and safety require an ever increasing need for reduction of impurities present in materials to be used in such applications.

Therefore, it is apparent that there is an ongoing need for the development of ethylene polymers having a high density, a low oxygen permeability and a low water vapour permeability, and also having a high purity.

This objective has now been achieved by an ethylene polymer comprising in the polymer chain recurring units according to Formula IB:

Formula IB

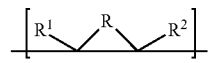

wherein R may for example be a moiety comprising ≥1 and ≤10 carbon atoms;

wherein $R^1$ and $R^2$ may be each individually hydrogen or a moiety comprising ≥1 and ≤5 carbon atoms, $R^1$ and $R^2$ may be the same or different;

wherein the ethylene polymer may for example have a molecular weight distribution defined as the ratio between the weight average molecular weight $M_w$ and the number average molecular weight $M_n$, ($M_w/M_n$) as determined according to ISO 16014-1 (2012) of ≥3.0 and ≤40.0;

the ethylene polymer may for example have a melting temperature as determined according to ISO 11357-3 (2011) at a heating rate of 10 K of ≥115° C.;

the ethylene polymer may for example have a density as measured according to ISO 1183-1 (2012), method A of ≥935 and ≤960 kg/m³;

the ethylene polymer may for example be essentially free from chromium, hafnium, zirconium and tetrahydrofuran;

for the fraction of the ethylene polymer having a molecular weight >100 kg/mol, the intrinsic viscosity of the ethylene polymer may for example be related to the molecular weight according to the inequality:

$$\log I.V. < 0.65 * \log M - 3.10$$

wherein I.V. is the intrinsic viscosity, expressed in dl/g, of a fraction of the ethylene polymer having a molecular weight M, the molecular weight M expressed in kg/mol;

wherein the molecular weight may be determined via Size Exclusion Chromatography (SEC) according to ISO 16014-1 (2012);

and wherein the intrinsic viscosity may be determined via differential viscometry of the fractions obtained from SEC, in accordance with ASTM D5225 (2014).

Ethylene polymers according to the invention may for example have improved barrier properties, such as for example low oxygen permeability and water vapour permeability. Such ethylene polymers for example have a high Vicat softening temperature. For example, such ethylene polymers have a high purity. Such ethylene polymers have an advantageous balance of processability and barrier properties, such as for example low oxygen permeability and water vapour permeability. Such advantageous balance of processability and barrier properties may for example result from a certain degree of long-chain branching in the ethylene polymers. Such ethylene polymers may for example have a high purity as they are essentially free from chromium, zirconium, hafnium and tetrahydrofuran.

Ethylene polymers according to the invention having such relation of the intrinsic viscosity to the molecular weight may for example have a high melt elasticity, low sagging, a low energy consumption in melt processing, a good bubble stability in blow film production, and good processability.

Alternatively, the present invention relates to an ethylene polymer wherein for the fraction of the ethylene polymer having a molecular weight >100 kg/mol, alternatively >200 kg/mol, alternatively >300 kg/mol, alternatively >400 kg/mol, alternatively >500 kg/mol, the intrinsic viscosity of the ethylene polymer is related to the molecular weight according to the inequality:

$$\log I.V. < 0.60 * \log M - 2.85$$

In the context of the present invention, recurring units are to be understood to be units of the polymer molecule that together form the polymer chain. Such units may for example be originating from unsaturated monomers comprising at least one carbon-carbon double bond capable of reacting in free-radical polymerisation reactions. For example, such unsaturated monomers may be olefinic monomers. Such free-radical addition polymerisation mechanisms are well known in the art and for example described in 'Introduction to Polymer', Young et al, Chapman & Hall, 1995, p. 43-68.

The molecular weight may be determined via Size Exclusion Chromatography (SEC) using for example a Polymer Laboratories PL-GPC220 high-temperature GPC/SEC system, to obtain fractions of the ethylene polymer having a certain molecular weight. For example, as column set may be used three Polymer Laboratories 13 μm PLgel Olexis, 300×7.5 mm. For example, the calibration for the molar mass may be performed with a linear polyethylene as standard. The molecular weight may be determined according to ISO 16014-1 (2012).

The intrinsic viscosity of the obtained fractions may be determined using a Polymer Laboratories BV-400 viscometer. Refractive index detector: Polymer Char IR5 infrared detector. The intrinsic viscosity may be determined in accordance with ASTM D5225 (2014).

In an embodiment, the ethylene polymers comprising recurring units derived from cyclic olefin comonomers according to the present invention may for example be produced in a high-pressure free-radical polymerisation process.

In an embodiment, the present invention relates to an ethylene polymer wherein R may for example be a moiety selected from linear alkanes, branched alkanes, cyclic alkanes, linear alkenes, branched alkenes or cyclic alkenes.

For example, R may be a linear alkane having 4 carbon atoms. Alternatively, R may be a linear alkane having 6 carbon atoms.

The present invention further relates to an ethylene polymer wherein R may for example be a moiety selected from —$C_2H_4$—, —$C_3H_6$—, —$C_4H_8$—, —$C_5H_{10}$—, —$C_6H_{12}$—.

The present invention also relates to an ethylene polymer wherein the ethylene polymer may for example be produced by reacting a reaction mixture comprising ethylene and one or more cyclic olefin comonomers.

The present invention also relates to an ethylene polymer wherein the ethylene polymer may for example comprise ≥0.05% and ≤6.00% of moieties according to formula I compared to the total number of recurring moieties in the ethylene copolymer.

For example, the ethylene comprises ≥0.05%, alternatively ≥0.10%, alternatively ≥0.20%, alternatively ≥0.30%, alternatively ≥0.50% of moieties according to formula I compared to the total number of recurring moieties in the ethylene copolymer.

For example, the ethylene comprises ≤6.00%, alternatively ≤4.00%, alternatively ≤3.00%, alternatively ≤2.00%, alternatively ≤1.00% of moieties according to formula I compared to the total number of recurring moieties in the ethylene copolymer.

For example, the ethylene comprises ≥0.05% and ≤6.00%, alternatively ≥0.10% and ≤3.00%, alternatively ≥0.20% and ≤2.00%, of moieties according to formula I compared to the total number of recurring moieties in the ethylene copolymer.

In an embodiment, the ethylene polymers according to the present invention are produced using at least ethylene and at least one cyclic olefin comonomer as feeds.

The cyclic olefin comonomers that may be used in the production of the ethylene polymers according to the present invention may for example be selected from compounds represented by the molecular structure of Formula II:

Formula II

In which R is a moiety comprising ≥1 and ≤10 carbon atoms;

In an embodiment, the present invention relates to an ethylene polymer wherein the cyclic olefin comonomer may for example be one or more selected from cyclobutene, cyclopentene, cyclohexene, cycloheptene, cyclooctene, cyclooctadiene, cyclononene, cyclodecene, 1-methyl cyclohexene, 3-methyl cyclohexene, α-pinene, and/or norbornene.

In an embodiment, the present invention relates to an ethylene wherein reaction mixture may for example comprise ≥0.10 and ≤2.00 mol % of the cyclic olefin comonomer compared to the total molar composition of the reaction mixture.

For example, the reaction mixture may comprise ≥0.10 mol %, alternatively 0.20 mol %, alternatively ≥0.30 mol % of the cyclic olefin comonomer, compared to the total molar composition of the reaction mixture.

For example, the reaction mixture may comprise ≤2.00 mol %, alternatively ≤1.00 mol %, alternatively ≤0.50 mol % of the cyclic olefin comonomer, compared to the total molar composition of the reaction mixture.

For example, the reaction mixture may comprise ≥0.10 mol % and ≤2.00 mol %, alternatively ≥0.20 mol % and ≤1.00 mol %, alternatively ≥0.30 mol % and ≤0.50 mol % of the cyclic olefin comonomer, compared to the total molar composition of the reaction mixture.

The reaction mixture is to be understood to be the total quantity of olefin monomers fed to the polymerisation reaction.

In an embodiment, such cyclic olefin comonomers may be monocyclic olefin comonomers. Examples of such monocyclic olefin comonomers include unsubstituted monocyclic olefins such as cyclobutene, cyclopentene, cyclohexene, cycloheptene, cyclooctene, cyclononene, and cyclodecene.

Examples of such monocyclic olefin comonomers include substituted monocyclic olefins. For example, such substituted monocyclic olefins may be monosubstituted, disubstituted or trisubstituted. For example, such substituted monocyclic olefins may comprise as substituents one or more of each a methyl, ethyl and/or butyl group.

Alternatively, such cyclic olefin comonomers may be multicyclic olefin comonomers. Examples of such multicyclic olefin comonomers include norbornene.

The cyclic olefin comonomers may for example comprise a single vinylic unsaturation in the cyclic structure. Alternatively, the cyclic olefin comonomers may for example comprise multiple vinylic unsaturations in the cyclic structure, such as two vinylic unsaturations. For example the cyclic olefin comonomers comprising multiple vinylic unsaturations may be a cyclic diene. For example, such cyclic diene may be cyclooctadiene.

For example, the cyclic olefin comonomer may be cyclohexene, cyclooctene or cyclooctadiene.

The objective can also be obtained by an ethylene polymer comprising in the polymer chain recurring units according to Formula I:

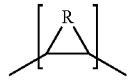

Formula I wherein R may for example be a moiety comprising ≥1 and ≤10 carbon atoms;
wherein
  the ethylene polymer may for example have a molecular weight distribution defined as the ratio between the weight average molecular weight $M_w$ and the number average molecular weight $M_n$, ($M_w/M_n$) as determined according to ASTM D-6474 (2012) of ≥3.0 and ≤13.0;
  the ethylene polymer may for example have a melting temperature as determined according to ISO 11357-3 (2011) at a heating rate of 10 K of ≥115° C.;
  the ethylene polymer may for example have a density as measured according to ISO 1183-1 (2012), method A of ≥935 and ≤960 kg/m³;
  the ethylene polymer may for example be essentially free from chromium, hafnium, zirconium and tetrahydrofuran;
  for the fraction of the ethylene polymer having a molecular weight >100 kg/mol, the intrinsic viscosity of the ethylene polymer may for example be related to the molecular weight according to the inequality:

$$\log \text{I.V.} < 0.65 * \log M - 3.10$$

wherein I.V. is the intrinsic viscosity, expressed in dl/g, of a fraction of the ethylene polymer having a molecular weight M, the molecular weight M expressed in kg/mol;
  wherein the molecular weight may be determined via Size Exclusion Chromatography (SEC) according to ISO 16014-1 (2012);
  and wherein the intrinsic viscosity may be determined via differential viscometry of the fractions obtained from SEC, in accordance with ASTM D5225 (2014).

Ethylene polymers according to the present invention may for example be produced in a high-pressure free radical polymerisation process. Such polymerisation process may for example be conducted in an autoclave reactor. Such autoclave reactor may for example be a reactor such as described in Nexant PERP Report 2013-2, 'Low Density Polyethylene', pages 48-63.

Alternatively, such polymerisation process may for example be conducted in a tubular reactor. Such tubular reactor may for example be a reactor such as described in Nexant PERP Report 2013-2, 'Low Density Polyethylene', pages 31-48. Such tubular reactor may for example be operated at pressures ranging from 150 to 300 MPa. The tubular reactor may have a tube length of for example between 1500 and 3000 m. The tubular reactor may for example have a ratio of length to inner diameter of ≥500:1, alternatively ≥1000:1, alternatively ≥5000:1. Such tubular reactors may for example have an inner tubular diameter of ≥0.01 m and ≤0.20 m, alternatively ≥0.05 m and ≤0.15 m.

For example, such high-pressure free radical polymerisation process comprise more than one of said autoclave reactors and/or said tubular reactors, for example positioned in series. For example, such high-pressure free radical polymerisation process comprise two reactors in series. For example, the process may comprise a first polymerisation in an autoclave reactor and a further polymerisation in a tubular reactor. Alternatively, the process may comprise a first polymerisation in a tubular reactor and a further polymerisation in an autoclave reactor. Alternatively, the process may comprise a first polymerisation in a tubular reactor and a further polymerisation in a further tubular reactor. Alternatively, the process may comprise a first polymerisation in an autoclave reactor and a further polymerisation in an autoclave reactor.

The autoclave process and the tubular process result in different chain architecture (Tacx et al., Polymer, Vol. 39, 1998, p. 3109-3113) and different molecular weight distribution of the polymer (Kaltenbacher, TAPPI, Vol. 50, 1967, p. 20).

Polymerisation in a tubular reactor may for example have an advantage in that the consumption of utilities such as electricity and cooling water per quantity of ethylene polymer that is produce, is lower compared to polymerisation in autoclave reactors. Tubular reactors also have an advantage in that they may be built to produce larger quantities of ethylene polymer on annual basis, compared to autoclave reactors.

For example, the ethylene polymer may be produced in a polymerisation process at a pressure of ≥180 MPa and ≤400 MPa.

For example, the ethylene polymer is produced in a polymerisation process at a pressure of ≥180 MPa, alternatively ≥200 MPa, alternatively ≥220 MPa, alternatively ≥240 MPa, alternatively ≥260 MPa.

In an embodiment, the ethylene polymer may for example be produced in a tubular reactor. The tubular reactor may for example comprise an inlet and an outlet. The inlet may for example comprise a position for entering a first feed stream into the tubular reactor.

The first feed stream that is fed to the tubular reactor at the inlet of the tubular reactor may for example comprise ethylene and comonomers. The first feed stream that is fed to the tubular reactor at the inlet of the tubular reactor may for example comprise ≥80.00%, alternatively ≥85.00%, alternatively ≥90.00%, alternatively ≥95.00% by weight of ethylene, compared to the total weight of said first feed stream that is fed to the tubular reactor at the inlet of the tubular reactor. The first stream that is fed to the inlet of the tubular reactor may for example comprise ≤99.99%, alternatively ≤99.95%, alternatively ≤99.90%, alternatively ≤99.50% by weight of ethylene, compared to the total weight of said first feed stream that is fed to the tubular reactor at the inlet of the tubular reactor. For example, the first feed stream that is fed to the tubular reactor at the inlet if the tubular reactor may comprise ≥80.00% and ≤99.99%, alternatively ≥85.00% and ≤99.90%, alternatively ≥90.00% and ≤99.50% by weight of ethylene, compared to the total weight of said first feed stream that is fed to the tubular reactor at the inlet of the tubular reactor.

The first feed stream that is fed to the tubular reactor at the inlet of the tubular reactor may for example comprise ≤5.00%, alternatively ≤3.00%, alternatively ≤1.00%, alternatively ≤0.50%, alternatively ≤0.30% by weight of comonomers, compared to the total weight of said first feed stream that is fed to the tubular reactor at the inlet of the tubular reactor. The first feed stream that is fed to the inlet of the tubular reactor may for example comprise ≥0.01%, alternatively ≥0.02%, alternatively ≥0.05%, alternatively ≥0.10% by weight of comonomers, compared to the total weight of said first feed stream that is fed to the tubular reactor at the inlet of the tubular reactor. For example, the first feed stream that is fed to the tubular reactor at the inlet of the tubular reactor may comprise ≥0.01% and ≤5.00%, alternatively ≥0.05% and ≤1.00%, alternatively ≥0.10% and ≤0.50% by weight of comonomers, compared to the total weight of said first feed stream that is fed to the inlet of the tubular reactor.

The inlet for entering a first feed stream at the inlet of the tubular reactor may for example also be used to feed first additional compound streams to the tubular reactor. Such first additional compound streams may for example comprise initiators. Such initiators may for example be used to control the polymerisation. Such initiator may for example be an initiator composition comprising one or more selected from organic peroxides or azo compounds. Suitable organic peroxides may for example include diacyl peroxides, dialkyl peroxides, peroxymonocarbonates, peroxydicarbonates, peroxyketals, peroxyesters, cyclic peroxides, hydroperoxides. Suitable azo compounds may for example include 2,2'-azodi (isobutyronitrile), 2,2'-azodi(2-methylbutyronitrile), 1,1'-azodi(hexahydrobenzonitrile).

Examples of suitable diacyl peroxides are diisobutyryl peroxide, di(3,5,5-trimethylhexanoyl) peroxide, dilauroyl peroxide, didecanoyl peroxide, dibenzoyl peroxide.

Examples of suitable dialkyl peroxides are dicumyl peroxide, di(tert-butylperoxyisopropyl)benzene, 2,5-dimethyl-2,5-di(tert-butylperoxy)hexane, tert-butyl cumyl peroxide, 2,5-dimethyl-2,5-di(tert-butylperoxy)hexyne, di-tert-butyl peroxide, di-isononanoyl peroxide, di-tert-amyl peroxide, didecanoyl peroxide.

In an embodiment, the free radical initiator composition may for example comprise 2,5-dimethyl-2,5-di(tert-butylperoxy)hexane.

Examples of suitable peroxymonocarbonates are tert-amylperoxy 2-ethylhexyl carbonate, tert-butylperoxy isopropyl carbonate, tert-butylperoxy 2-ethylhexyl carbonate.

Examples of suitable peroxydicarbonates are di(3-methoxybutyl)peroxydicarbonate, di-sec-butyl peroxydicarbonate, diisopropyl peroxydicarbonate, di(4-tert-butylcyclohexyl) peroxydicarbonate, di(2-ethylhexyl) peroxydicarbonate, dibutyl peroxydicarbonate, diacetyl peroxy dicarbonate, dimyristyl peroxydicarbonate, dicyclohexyl peroxydicarbonate.

Examples of suitable peroxyketals are 1,1-di(tert-butyl peroxy)-3,5,5-trimethylcyclohexane, 1,1-di(tert-amyl peroxy)cyclohexane, 1,1-di(tert-butyl peroxy)cyclohexane, 2,2-di(tert-butyl peroxy)butane, butyl 4,4-di(tert-butyl peroxy)valerate, n-ethyl-4,4-di-(tert-butylperoxy)valerate, ethyl-3,3-di(tert-butylperoxy)butyrate, ethyl-3,3-di(tert-amylperoxy)butyrate.

Examples of suitable peroxyesters are cumyl peroxyneodecanoate, 1,1,3,3, -tetramethylbutylperoxyneodecanoate, cumyl peroxyneoheptanoate, tert-amyl peroxyneodecanoate, tert-butyl peroxyneodecanoate, tert-butyl peroxyisononanoate, tert-butyl permaleate, tert-butyl peroxydiethylisobutyrate, 1,1,3,3-tetramethylbutyl peroxypivalate, tert-butyl peroxyneoheptanoate, tert-amyl peroxypivalate, tert-butyl peroxypivalate, 2,5-dimethyl-2,5-di(2-ethylhexanoylperoxy)hexane, 1,1,3,3-tetramethylbutyl peroxy-2-ethylhexanoate, tert-amyl peroxy-2-ethylhexanoate, tert-butyl peroxy-2-ethylhexanoate, tert-butyl peroxydiethylacetate, tert-butyl peroxyisobutyrate, tert-amyl peroxyacetate, tert-butyl peroxy-3,5,5-trimethylhexanoate, tert-amyl peroxybenzoate, tert-butyl peroxyacetate, tert-butyl peroxybenzoate.

Examples of suitable cyclic peroxides are 3,6,9-triethyl-3,6,9-trimethyl-1,4,7-triperoxononane, 3,3,5,7,7-pentamethyl-1,2,4-trioxepane, 3,3,6,6,9,9,-hexamethyl-1,2,4,5-tetraoxacyclononane.

Examples of suitable hydroperoxides are isopropylcumyl hydroperoxide, 1,1,3,3-tetramethylbutyl hydroperoxide, cumyl hydroperoxide, tert-butyl hydroperoxide, tert-amyl hydroperoxide, methyl isobutyl ketone hydroperoxide, di-isopropyl hydroxyperoxide.

Such initiators may for example be fed to the tubular reactor in a pure form or as a solution in a solvent. As solvent, for example a $C_2$-$C_{20}$ normal paraffin or $C_2$-$C_{20}$ isoparaffin may be used. For example, such solution may comprise ≥2.0% and ≤65.0% by weight of initiator, alternatively ≥5.0% and ≤40.0% by weight, alternatively ≥10.0% and ≤30.0% by weight, compared to the total weight of the solution.

Such initiators may for example be introduced into the polymerisation reactor in quantities of ≤200 ppm, compared to the total weight of the materials fed to the polymerisation reactor.

Such first additional compound streams may for example comprise modifiers. Examples of such modifiers may include inhibitors, scavengers and/or chain regulators, such as aldehydes, ketones and aliphatic hydrocarbons. Examples of chain regulators are propene, propylene and propione aldehyde. Such modifiers may for example be fed to the tubular reactor in a pure form or as a solution in a solvent.

The tubular reactor may along the length of the reactor have multiple further feed inlets. Such further feed inlets may for example be used to feed further feed streams to the tubular reactor. Such further feed streams may for example have the same or different composition than the first feed stream. Such further feed streams may each have the same or different composition.

The further feed streams may for example comprise ethylene and comonomers. The further feed streams may for example comprise ≥80.00%, alternatively ≥85.00%, alternatively ≥90.00%, alternatively ≥95.00% by weight of ethylene, compared to the total weight of said further feed streams. The further feed streams may for example comprise ≤99.99%, alternatively ≤99.95%, alternatively ≤99.90%, alternatively ≤99.50% by weight of ethylene, compared to the total weight of said further feed streams. For example, the further feed streams may comprise ≥80.00% and ≤99.99%, alternatively ≥85.00% and ≤99.90%, alternatively ≥90.00% and ≤99.50% by weight of ethylene, compared to the total weight of said further feed streams.

The further feed streams may for example comprise ≤5.00%, alternatively ≤3.00%, alternatively ≤1.00%, alternatively ≤0.50%, alternatively ≤0.30% by weight of comonomers, compared to the total weight of said further feed streams. The further feed streams may for example comprise ≥0.01%, alternatively ≥0.02%, alternatively ≥0.05%, alternatively ≥0.10% by weight of comonomers, compared to the total weight of said further feed streams. For example, the further feed streams may comprise ≥0.01% and ≤5.00%, alternatively ≥0.05% and ≤1.00%, alternatively ≥0.10% and ≤0.50% by weight of comonomers, compared to the total weight of said further feed streams.

Such additional feed inlets may for example be used to feed further additional compound streams to the tubular reactor. Such further additional compound streams may for example be the same or different than the first additional compound streams. Such further additional compound streams may each have the same or different composition.

The free-radical addition polymerisation process of ethylene and cyclic olefin comonomers may be conducted using an initiator to support the formation of free radicals based on ethylene and/or the cyclic olefin comonomers. Such free-radical addition polymerisation process is an exothermic process. In the case that the polymerisation process for the production of ethylene polymers according to the present invention is performed in a tubular reactor, said tubular reactor may be provided with external cooling. Such external cooling may for example be performed via cooling jackets. Such cooling jackets may for example be operated using water as medium that removes heat from the tubular reactor.

The ethylene polymers comprising recurring units according to the present invention may for example have a density as measured according to ISO 1183-1 (2012), method A of ≥935 and ≤960 kg/m³. For example, the ethylene polymers according to the present invention may have a density of ≥930 kg/m³, alternatively ≥934 kg/m³, alternatively ≥935 kg/m³, alternatively ≥939 kg/m³, alternatively ≥940 k/m³, alternatively ≥944 kg/m³, alternatively ≥945 kg/m. For example, the ethylene polymers according to the present invention may have a density of ≤971 kg/m³, alternatively ≤970 kg/m³, alternatively ≤965 kg/m³, alternatively ≤960 kg/m³, alternatively ≤959 kg/m³ alternatively ≤955 kg/m³, alternatively ≤954 kg/m³. For example, the ethylene polymers according to the present invention may have a density of ≥930 kg/m³ and ≤970 kg/m³, alternatively ≥934 kg/m³ and ≤965 kg/m³, alternatively ≥939 kg/m³ and ≤959 kg/m³, alternatively ≥944 kg/m³ and ≤954 kg/m³.

The ethylene polymer may for example have a molecular weight distribution (MWD) defined as the ratio between the weight average molecular weight $M_w$ and the number average molecular weight $M_n$, ($M_w/M_n$) as determined according to ISO 16014-1 (2012) of 3.0, alternatively ≥4.0, alternatively ≥6.0. The ethylene polymer may for example have an MWD of ≤40.0, alternatively ≤30.0, alternatively ≤25.0. The ethylene polymer may for example have an MWD≥3.0 and ≤40.0, alternatively ≥6.0 and ≤30.0.

The ethylene polymer may for example have a molecular weight distribution, also referred to as MWD, as determined according to ISO 16014-1 (2012) of ≥3.0, alternatively ≥4.0, alternatively ≥6.0. The ethylene polymer may for example have an MWD of ≤13.0, alternatively ≤12.0, alternatively ≤11.0. The ethylene polymer may for example have an MWD ≥3.0 and ≤13.0, alternatively ≥6.0 and ≤12.0. Said MWD is defined as the ratio between the weight average molecular weight $M_w$ and the number average molecular weight $M_n$, ($M_w/M_n$) as determined according to ISO 16014-1 (2012).

In an embodiment, the present invention relates to a polymer composition that may for example comprise an ethylene polymer according to the present invention. Such polymer composition may for example comprise ≥50.0 wt %, alternatively ≥75 wt %, alternatively ≥90 wt %, alternatively ≥95 wt % of the ethylene polymer, compared to the total weight of the polymer composition.

Furthermore, the present invention relates to a film that may for example comprise an ethylene polymer according to the present invention.

The invention further relates to a package for fresh food products that may for example comprise a layer comprising an ethylene polymer according to the present invention.

Packages for example include packages for fresh food products, such as for example fruit juices, dairy products, meat, cheese, fish, fruits, vegetables and/or baked goods.

In an embodiment, said layer may for example comprise ≥80.0% by weight of an ethylene polymer according to any one of claims 1-9 compared to the total weight of said layer. In an embodiment, said layer may for example be present in the form of one or more of a single-layer film, one or more layer(s) of a multi-layer film, and/or an extrusion-coated film.

Single-layer or multi-layer films may for example be produced by blown film production or cast film production. Both processes are known in the art and described in e.g. the Handbook of Plastic Films, E. M Abdel-Bary (ed.), Rapra Technology Ltd., 2003, in sections 2.3 and 2.4. The film according to the present invention may be produced via either blown film production or cast film production. Such films may for example be flexible films. Such films may for example have a thickness of ≤200.0 µm, alternatively ≤100.0 µm, alternatively ≤50.0 µm, alternatively ≤25.0 µm.

Extrusion-coated films may for example be produced by deposition of a layer of molten material onto a substrate, followed by cooling of the molten material for form a layer adhering to the substrate. For example, the molten material may comprise the ethylene polymer according to the present invention. For example, the substrate may be paper, paperboard, cardboard, foils such as aluminium foils, and/or polymer films such as polyamide films and/or EVOH films. For example, the substrate may have a top planar surface onto which the layer of ethylene polymer is deposited and a bottom planar surface. For example, such layer may have a thickness of 3.0 to 50.0 µm, for example 5.0 to 25.0 µm. For example, said layer of molten material may be deposited by extruding the molten material onto a substrate onto the top planar surface wherein the substrate is guided by a pressure roll contacting the bottom planar surface, and wherein the substrate, following deposition of the molten material, is on the side of the top planar surface contacted by a cooling cylinder that reduces the temperature of the deposited material to a temperature below the softening temperature of the deposited material.

The ethylene polymers according to the present invention have for example a low permeability to oxygen and water vapour. In the context of the present invention, permeability is to be understood to be the degree to which a film comprising at least one layer of the ethylene polymer, for example a single-layer film or a multilayer film, enables molecules of certain defined compounds to pass through said film, for example by means of diffusion. For example, such compound may be oxygen. Alternatively, such compound may be water, for example in the form of water vapour. Certain applications of films may require a certain oxygen permeability. Certain applications of films may require a certain water vapour permeability. Oxygen permeability is expressed as oxygen transmission rate determined in accordance with ISO 15105-2 (2003), method A. Water vapour permeability is expressed as water vapour transmission rate determined in accordance with ISO 15106-3 (2003).

The invention will now be illustrated by the following non-limiting examples.

EXPERIMENT I

Preparation Of Ethylene Polymer

In a high-pressure polymerisation reactor, an ethylene polymer was prepared by reacting a reaction mixture comprising ethylene an amount of comonomer. The comonomer was fed as a 1.45 mol % solution in isopropyl alcohol. The reaction was performed at a pressure of 200 MPa. The reaction temperature was kept between 200 and 230° C. The reaction was initiated by addition of a solution of t-butyl peroxy pivalate in heptane. The obtained ethylene polymer was collected. The examples were prepared using different comonomers and quantities as presented in Table I:

TABLE I

|  | Ethylene polymer A | Ethylene polymer B | Ethylene polymer C |
|---|---|---|---|
| Comonomer | cyclohexene | cyclooctene | cyclooctene |
| Comonomer feed concentration | 0.2 mol % | 0.7 mol % | 0.2 mol % |
| Initiator feed concentration | 0.00153 mol % | 0.00179 mol % | 0.00250 mol % |

Wherein the mol % is to be understood to be the fraction in mol % compared to the total quantity of reactive ingredients fed to the reaction. The reactive ingredients in the above examples are ethylene, comonomer and initiator.

EXPERIMENT II

Determination Of Intrinsic Viscosity And Molecular Weight

Ethylene polymer A, B and C according to the invention as obtained in experiment I and for comparative purposes ethylene polymer D, a commercial polyethylene material grade 0863F, obtainable from SABIC, ethylene polymer E, a commercial polyethylene material grade LDPE 1922, and ethylene polymer F, a commercial polyethylene material grade ICP4907S, all obtainable from SABIC, were subjected to Size Exclusion Chromatography (SEC) using a Polymer Laboratories PL-GPC220 high-temperature GPC/SEC system, to obtain fractions of the ethylene polymer having a certain molecular weight. The column set used are three Polymer Laboratories 13 µm PLgel Olexis, 300×7.5 mm. The calibration for the molar mass was performed with a linear polyethylene as standard. The molecular weight was determined according to ISO 16014-1 (2012).

The intrinsic viscosity of these fractions was subsequently determined using a Polymer Laboratories BV-400 viscometer. Refractive index detector: Polymer Char IR5 infrared detector. The intrinsic viscosity was determined in accordance with ASTM D5225 (2014).

Results are presented in Table II.

TABLE II

| Molecular weight (kg/mol) | Intrinsic viscosity (dl/g) Ethylene polymer | | | | | |
|---|---|---|---|---|---|---|
|  | A | B | C | D | E | F |
| 10 | 0.292 | 0.292 | 0.288 | 0.348 | 0.341 | 0.371 |
| 50 | 0.809 | 0.800 | 0.742 | 1.055 | 0.803 | 1.085 |
| 100 | 1.174 | 1.138 | 1.033 | 1.820 | 1.127 | 1.846 |
| 200 | 1.585 | 1.482 | 1.298 | 3.020 | 1.471 | 3.007 |
| 300 | 1.904 | 1.731 | 1.489 | 4.064 | 1.686 | 4.014 |
| 400 | 2.133 | 1.914 | 1.589 | 5.023 | 1.845 | 4.908 |
| 500 | 2.540 | 2.136 | 1.692 | 5.840 | 1.982 | 5.741 |
| 600 | 2.833 | 2.405 | 1.777 | 6.194 | 2.090 | 6.472 |

EXPERIMENT III

Determination of Material Properties

Material properties of the sample ethylene polymers A-F were determined. The results are presented in Table III.

TABLE III

| Property (Unit) | Method | Ethylene polymer | | | | | |
| --- | --- | --- | --- | --- | --- | --- | --- |
| | | A | B | C | D | E | F |
| Melting temperature (° C.) | ISO 11357-3 (2011) heating rate 10 K. | 115 | 116 | 118 | 134 | 112 | 131 |
| Density (kg/m$^3$) | ISO 1183-1 (2012), method A | 936 | 938 | 940 | 964 | 926 | 949 |
| Transparency (%) | ASTM D1746 (2015) | | 92 | 90 | | 86 | |
| Water vapour transmission rate (g/(m$^2$*24 h)) | ISO 15106-3 (2003) | 0.9 | 1.1 | 1.1 | 4.0 | 1.8 | 2.3 |
| Oxygen transmission rate (cm$^3$/(m$^2$*bar*24 h)) | ISO 15105-2 (2003), method A | 1335 | 1474 | 2135 | 1000 | 6389 | 1339 |
| Molecular Weight Distribution (—) | ISO 16014-1 (2012) | 3.7 | 4.4 | 9.9 | 5.3 | 21.7 | |

ISO 16014-1 (2012) relates to determination of average molecular mass and molecular mass distribution using size-exclusion chromatography.

ISO 11357-3 (2011) relates to determination of temperature and enthalpy of melting and crystallisation via differential scanning calorimetry.

ISO 1183-1 (2012) relates to determination of density of non-cellular plastics.

ISO 15106-3 (2003) relates to determination of water vapour transmission rate of film and sheeting.

ISO 15105-2 (2003) relates to determination of gas transmission rate of film and sheeting.

ASTM D-5225 (2014) relates to a standard test method for measuring solution viscosity of polymers with a differential viscometer.

ASTM D6474 (2012) relates to a standard test method for determining molecular weight distribution and molecular weight averages of polyolefins by high temperature gel permeation chromatography.

ASTM D1746 (2015) relates to a standard test method for transparency of plastic sheeting.

From the results obtained in experiments II and III, it becomes apparent that ethylene polymers according to the present invention having a high density, high purity and good processability, whilst maintaining barrier properties for oxygen and water vapour at a level similar to high-density polyethylenes produced via catalytic processes.

The invention claimed is:

1. The ethylene polymer comprising moieties according to Formula IB:

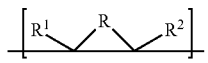

Formula IB wherein R is a moiety comprising ≥1 and ≤10 carbon atoms;

wherein $R^1$ and $R^2$ are each individually hydrogen or a moiety comprising ≥1 and ≤5 carbon atoms, $R^1$ and $R^2$ may be the same or different;
wherein
the ethylene polymer has a molecular weight distribution defined as the ratio between the weight average molecular weight $M_w$ and the number average molecular weight $M_n$, ($M_w/M_n$) as determined according to ISO 16014-1 (2012) of ≥3.0 and ≤40.0;
the ethylene polymer has a melting temperature as determined according to ISO 11357-3 (2011) at a heating rate of 10 K per minute of ≥115° C.;
the ethylene polymer has a density as measured according to ISO 1183-1 (2012), method A of ≥935 and ≤960 kg/m$^3$;
the ethylene polymer is essentially free from chromium, hafnium, zirconium and tetrahydrofuran;
for the fraction of the ethylene polymer having a molecular weight >100 kg/mol, the intrinsic viscosity of the ethylene polymer is related to the molecular weight according to the inequality:

$$\log \text{I.V.} < 0.65 * \log M - 3.10$$

wherein I.V. is the intrinsic viscosity, expressed in dl/g, of a fraction of the ethylene polymer having a molecular weight M, the molecular weight M expressed in kg/mol;
wherein the molecular weight is determined via Size Exclusion Chromatography (SEC) according to ISO 16014-1 (2012);
and wherein the intrinsic viscosity is determined via differential viscometry of the fractions obtained from SEC, in accordance with ASTM D5225 (2014).

2. The ethylene polymer according to claim 1, wherein R is a moiety selected from linear alkanes, branched alkanes, cyclic alkanes, linear alkenes, branched alkenes or cyclic alkenes.

3. The ethylene polymer according to claim 1, wherein R is a moiety selected from —$C_2H_4$—, —$C_3H_6$—, —$C_4H_8$—, —$C_5H_{10}$—, —$C_6H_{12}$—.

4. The ethylene polymer according to claim 1, wherein the ethylene polymer is produced in a polymerisation process at a pressure of ≥180 MPa and ≤400 MPa.

5. The ethylene polymer according to claim 1, wherein the ethylene polymer is produced in a tubular reactor.

6. The ethylene polymer according to claim 1, wherein the ethylene polymer is produced by reacting a reaction mixture comprising ethylene and one or more cyclic olefin comonomers.

7. The ethylene polymer according to claim 6, wherein the cyclic olefin comonomer is one or more selected from cyclobutene, cyclopentene, cyclohexene, cycloheptene, cyclooctene, cyclooctadiene, cyclononene, cyclodecene, 1-methyl cyclohexene, 3-methyl cyclohexene, α-pinene, and/or norbornene.

8. The ethylene polymer according to claim 6, wherein the reaction mixture comprises ≥0.10 and ≤2.00 mol % of the cyclic olefin comonomer compared to the total molar composition of the reaction mixture.

9. The ethylene polymer according to claim 1, wherein the ethylene polymer comprises ≥0.05 and ≤6.00% of moieties according to formula I compared to the total number of recurring moieties in the ethylene copolymer.

10. A polymer composition comprising an ethylene polymer according to claim 1.

11. A film comprising an ethylene polymer according to claim 1.

12. A package for fresh food products comprising a layer comprising an ethylene polymer according to claim 1.

13. The package according to claim 12, wherein said layer comprises ≥80.0% by weight of the ethylene polymer compared to the total weight of said layer.

14. The package according to claim 12, wherein said layer is present in the form of one or more of a single-layer film, one or more layer(s) of a multi-layer film, and/or an extrusion-coated film.

\* \* \* \* \*